United States Patent [19]
Barath et al.

[11] Patent Number: 4,754,328
[45] Date of Patent: Jun. 28, 1988

[54] LASER ENDOSCOPE

[75] Inventors: James D. Barath, Parker, Colo.; Steven K. Case, St. Louis Park, Minn.

[73] Assignee: Medical Dynamics, Inc., Englewood, Colo.

[21] Appl. No.: 836,344

[22] Filed: Mar. 5, 1986

Related U.S. Application Data

[62] Division of Ser. No. 567,800, Jan. 3, 1984, Pat. No. 4,589,404.

[51] Int. Cl.$^4$ .......................... A61B 1/04; A61B 1/06; G02B 6/26; H04N 7/18
[52] U.S. Cl. ........................................ 358/98; 128/6; 350/96.22; 350/96.26; 358/901
[58] Field of Search ...................... 358/98, 901; 128/6, 128/7, 8; 350/96.22, 96.26

[56] References Cited

U.S. PATENT DOCUMENTS

| | | | |
|---|---|---|---|
| 3,858,577 | 1/1975 | Bass | 128/4 |
| 4,011,403 | 3/1977 | Epstein | 358/98 |
| 4,313,431 | 2/1982 | Frank | 128/7 |
| 4,325,606 | 4/1982 | Ikuno | 350/96.26 |
| 4,475,539 | 10/1984 | Konomura | 128/6 |
| 4,539,586 | 9/1985 | Danna | 358/98 |
| 4,590,923 | 5/1986 | Watanabe | 358/98 |

Primary Examiner—Howard W. Britton
Attorney, Agent, or Firm—Fields, Lewis, Pittenger & Rost

[57] ABSTRACT

A laser endoscope includes a micro-thin optic cable assembly which may be inserted into a body cavity by micro-surgical or non-surgical procedures. A coherent jacketed fiber optical bundle is provided in the center of the assembly having a diameter of no more than 3.5 mm. with an optical lens system at the distal end for reflecting an image of a portion of the interior of the cavity. A pair of single optical fibers are spirally wound around the cable, each of which has a total diameter including a jacket of approximately 140 microns. One of these fibers carries a laser light beam to the cavity and the other is for redundancy. The proximate end of the optical cable assembly connects to a remote unit wherein a laser diode light source is provided to direct a beam of light into the end of one of the single optical fibers. A TV camera is also provided in the remote unit together with suitable optics for transmitting the image from the optical cable to a viewing screen on the remote unit.

15 Claims, 7 Drawing Sheets

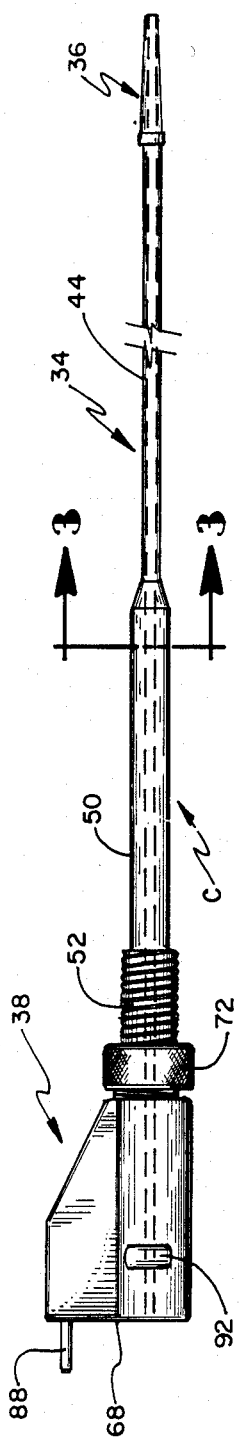
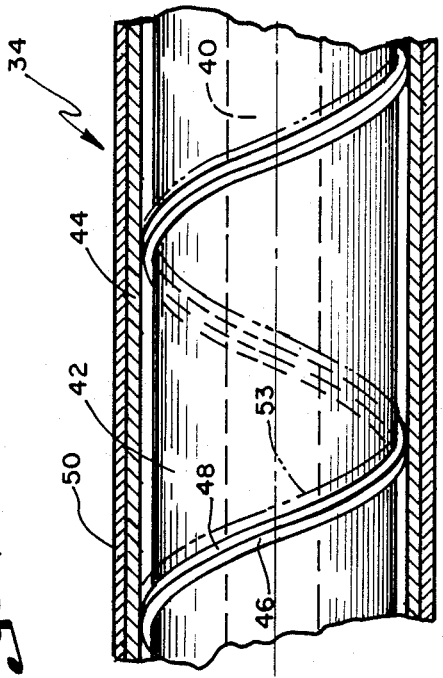
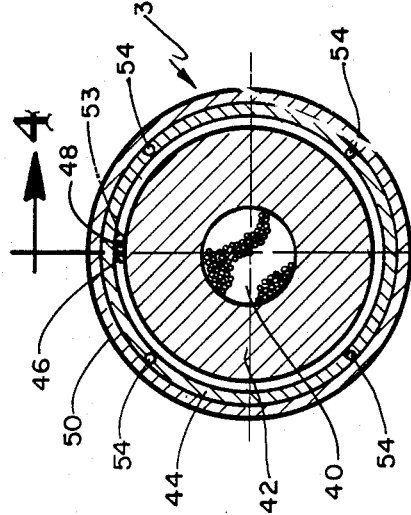

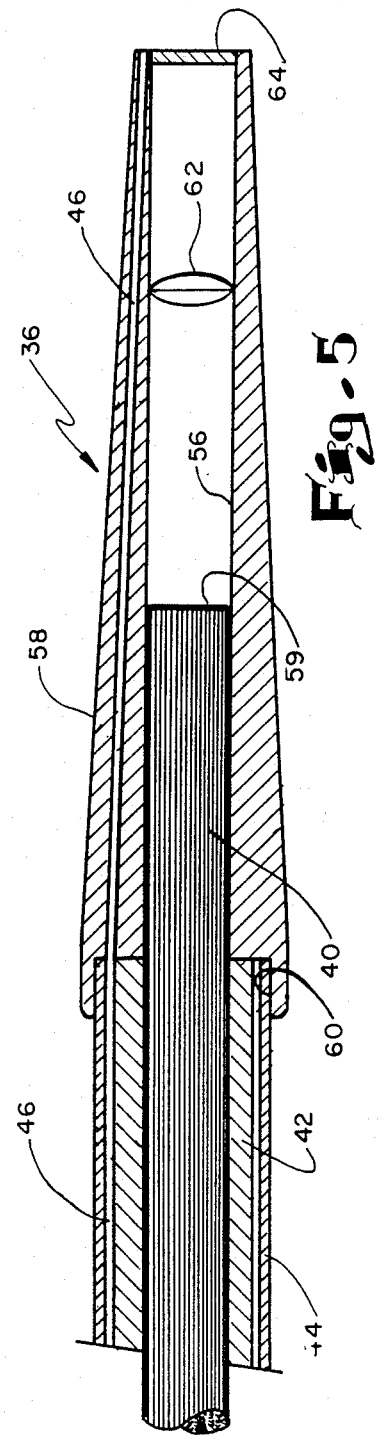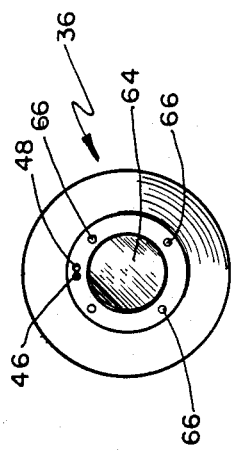

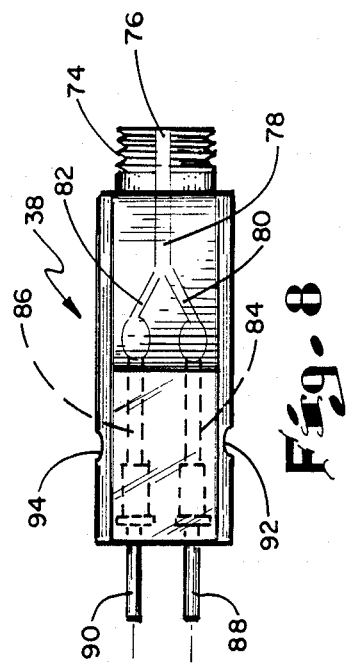
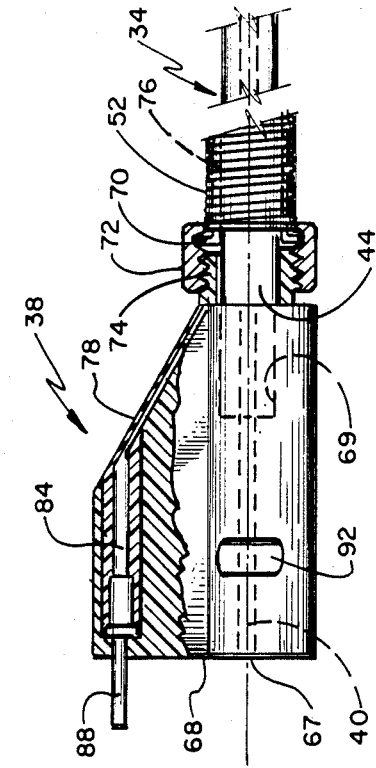
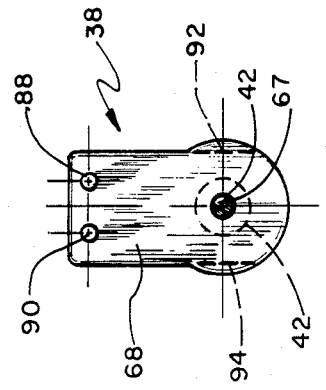

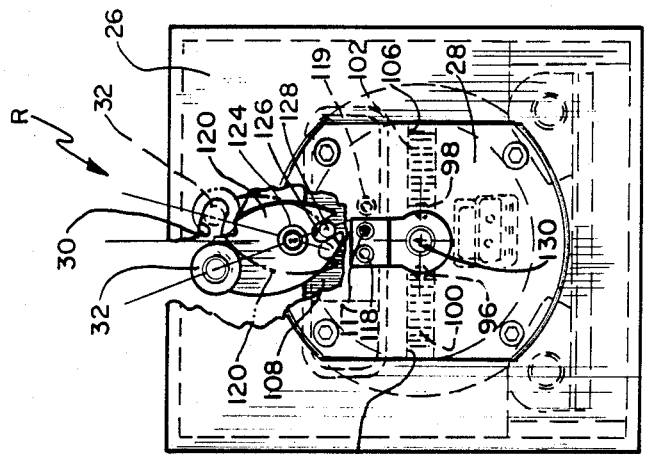
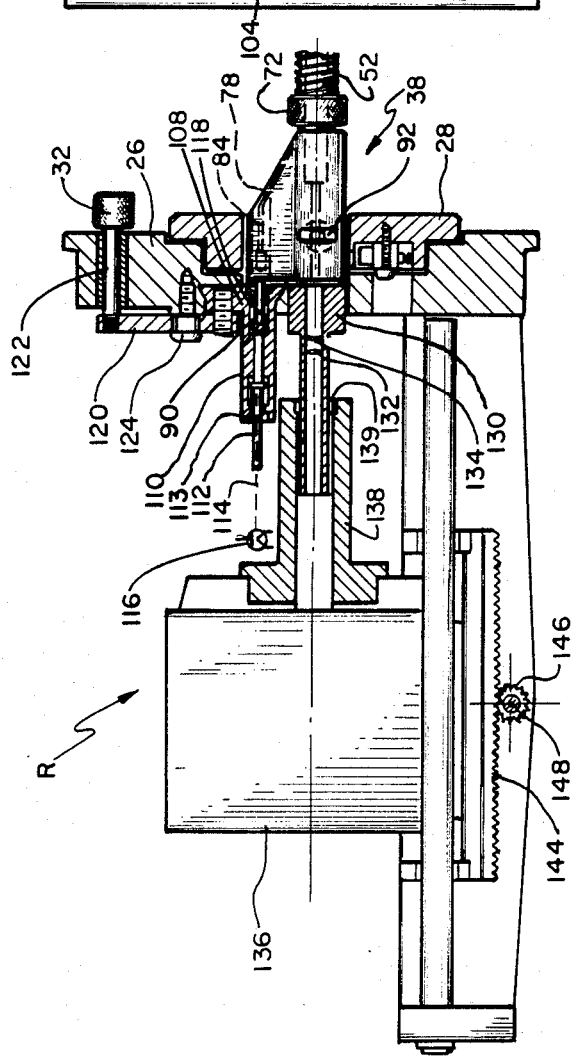
Fig-11
Fig-10

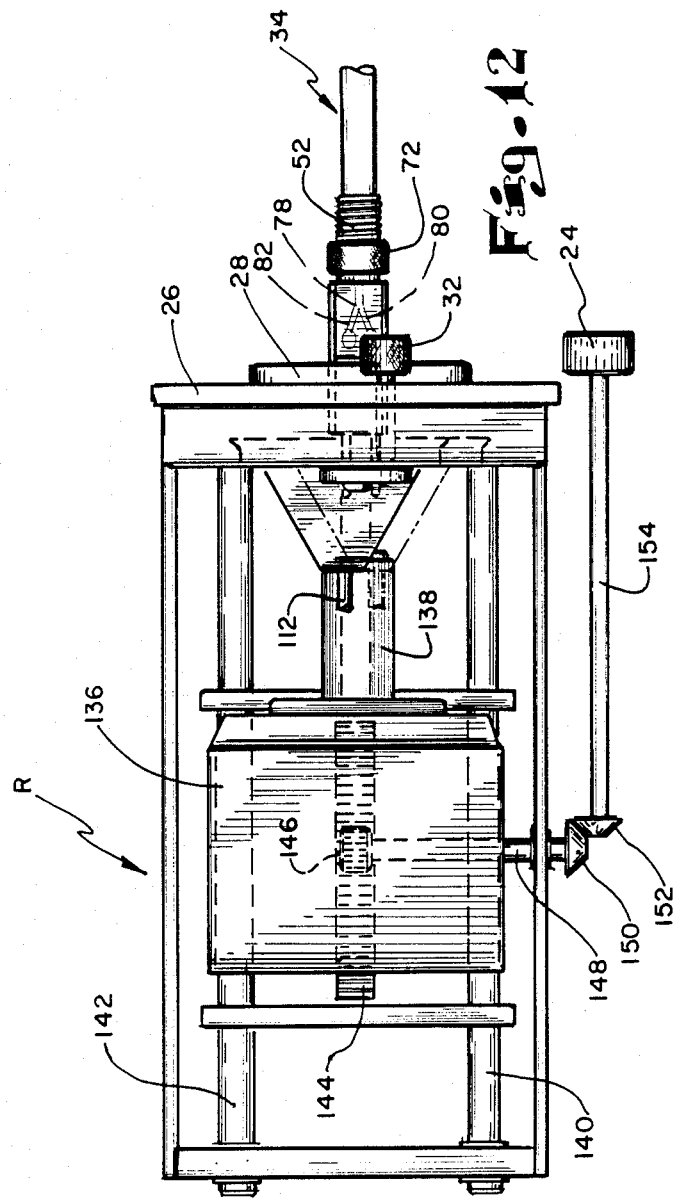

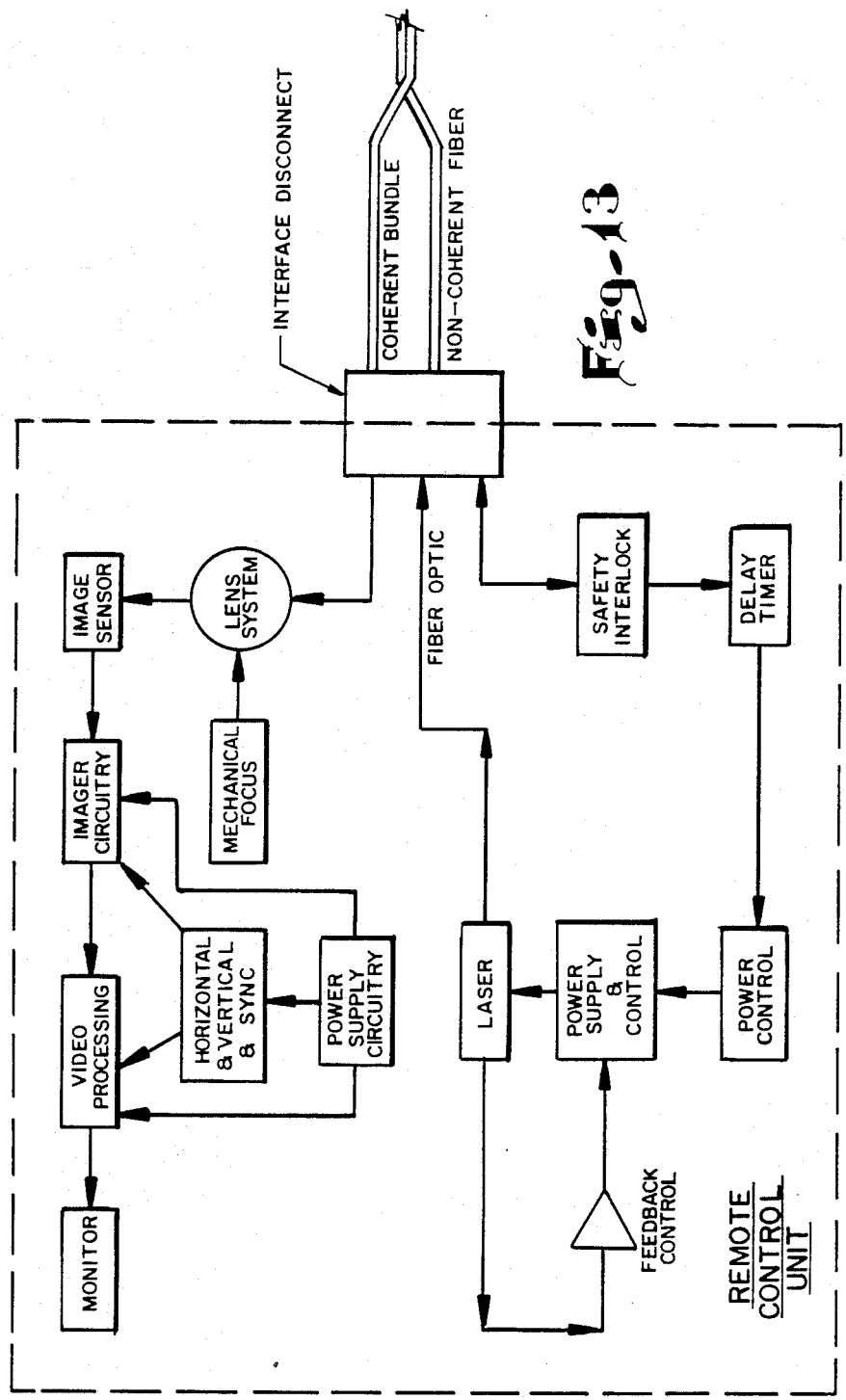

LASER ENDOSCOPE

This is a division, of the application Ser. No. 567,800 filed Jan. 3, 1984, now U.S. Pat. No. 4,589,404.

TECHNICAL FIELD

This invention relates to a laser endoscope, and more particularly to such an endoscope of micro-thin dimensions wherein a single optical fiber is used to transmit a laser light beam to a site in a body cavity and a coherent optical fiber bundle transmits a reflected image for viewing on a video screen or monitor.

BACKGROUND ART

Prior to this invention, laser light beams have been used both for illumination and for treatment of disease in patients. However, most of these instruments have not been of sufficiently small size that they can be passed through the various canals and openings of the body without discomfort to the patient and in some cases surgical procedures are required for introducing the instrument to the desired location within a body cavity. No device is known which can be inserted into a body cavity through the canals of the body which minimizes discomfort to the patient to the point of being nearly nonexistent or which can be introduced into the body cavities by use of a needle so as to obviate the necessity for a conventional surgical procedure.

U.S. Pat. No. 3,858,577 to Bass et al. discloses an endoscope of substantial size for performing laser surgery. In this device, a conventional light is used through fiber optics to illuminate the operating site g and laser light is used to perform a surgical procedure.

U.S. Pat. No. 4,011,403 to Epstein, et al. discloses a fiber optic laser endoscope. The device utilizes a laser beam as a light source and an optical fiber as a light transmitter. The sensing means includes a TV camera located at the investigated site. The laser beam produces three different wavelengths which produce white light. Also ultraviolet or infrared light can be used. The camera is separate from the fiber optics and the laser.

U.S. Pat. No. 4,313,431 to Frank discloses an endoscope deploying a laser light source with a light conducting fiber. This device is used for irradiating bladder tumors utilizing the laser light beam.

DISCLOSURE OF THE INVENTION

This invention relates to an apparatus for viewing or treatment within a body cavity by non-surgical or micro-surgical procedures. This apparatus comprises a coherent optical fiber bundle in an optical cable whose diameter is micro-thin and has a planar distal end for insertion into a body cavity and a planar proximate end. A single optical fiber having a distal end adjacent to the distal end of the cable and a proximate end adjacent the proximate end of the cable is also provided. A laser light source is alignable with the proximate end of the single fiber to transmit light to the distal end to illuminate the body cavity. Optical lens means at the distal end of the optical cable, focus an image of a portion of the cavity on the distal end of the optical cable for transmission therethrough. Optic focus means are connectable to the proximate end of the optical cable to focus an image of a portion of the body cavity reflected through the cable and viewing means are connected to the focus means for displaying an image of the desired portion of the body cavity.

More particularly, the laser endoscope includes a remote viewing unit which includes a TV camera, a viewing monitor for displaying an image of the image viewed by the TV camera, an optical cable interface including optical focus means for focusing an image from an optical cable on the TV camera, a laser diode for providing a beam of light to an optical fiber and a laser fiber interface for aligning the light beam from the laser diode with the optical fiber. In addition, the endoscope includes an optical cable assembly which includes a coherent fiber optical bundle of micro-thin diameter having a planar distal end for insertion into the body and a planar proximate end. An optical lens means at the distal end of the cable assembly is provided to focus an image of a portion of the cavity on the distal end of the optical cable for transmission therethrough. A single optical fiber having a distal end adjacent the distal end of the bundle and a proximate end adjacent the proximate end of the bundle is provided within the cable assembly. Finally, an interface connector removably connects the remote viewing unit for aligning the optical bundle with the optical cable interface and for aligning the single optical fiber with the laser fiber interface.

A stationary optical system can be provided within the remote unit and aligned with the optical bundle and means can be provided to adjust the focus of the camera with respect to the stationary optical system for projecting a properly defined image onto the viewing monitor.

Additionally, a redundant optical fiber, identical in size and location to the single optical fiber, can be provided for redundancy. The interface connector is provided with a pair of spaced optic fiber pins aligned respectively with the ends of the single optic fiber and the redundant fiber. Socket means are provided in the laser fiber interface for selectively receiving one of the optic fiber pins and aligning it with the beam of light from the laser diode. Means are also provided for selectively shifting the socket means for alignment with the desired one of the pins prior to insertion of the interface connector. This shifting means may take the form of a slide member supporting the socket means and mounted for sliding movement on the remote unit from a first position to locate the socket means to receive the optic fiber pin to align the single optic fiber with the beam of light from the laser diode to a second position to locate the socket means to receive the redundant fiber pin to align the redundant optic fiber with the beam of light from the laser diode. This device may be operated by a suitable lever means connected to the slide.

The cable assembly, if desired, can have a plurality of tubular passageways extending along the optical cable for supplying a fluid to temporarily clear away blood or other body fluids at the viewing site within the body cavity to enhance viewing. Conveniently, these passageways may be equally spaced around the optical cable.

Conveniently, the suitable jackets may be provided around both the optical cable and the single fibers. Additionally, a tubular tip can be provided having a central passageway with the distal end of the optical cable extending through the center of the tip and into the interior thereof. The single fiber and redundant fiber can also extend through side passageways offset from the tubular center of the tip to the distal end of the tip. A lens system can be provided within the tubular tip between the distal end of the optical cable and the distal end of the tip. Conveniently, the tubular tip may be tapered toward its distal end to facilitate insertion into a body cavity.

Also it will be understood that these single fibers could comprise fibers through the center of the optical cable rather than being separate fibers which are spirally wound around the outside of the cable. Also, additional fibers could be used for transmitting light from a different laser light source, such as an argon laser or YAG laser for laser surgery such as cauterizing tissue or for destroying tumors and other undesirable body growths such as kidney stones and gall stones. It could also be used for destroying placque within an artery, and particularly arteries near the heart.

From the foregoing, the advantages of this invention will become readily apparent, when taken in conjunction with the description of the drawings which follows.

BRIEF DESCRIPTION OF THE DRAWINGS

FIG. 2 is a fragmentary side perspective view of the optical cable assembly of FIG. 1;

FIG. 3 is a greatly enlarged, vertical section, taken along lines 3—3 of FIG. 2 showing details of the internal structure of the optical cable assembly;

FIG. 4 is a vertical section, taken along lines 4—4 of FIG. 3, showing the spiral wrapping of the laser light carrying single optical fibers;

FIG. 5 is an enlarged longitudinal section of the distal end of the optical cable assembly of FIG. 2;

FIG. 6 is an end elevation of the distal end of the cable assembly shown in FIG. 5;

FIG. 7 is an enlarged fragmentary side elevational view of the interface connector on the cable assembly of FIG. 2, with parts broken away for clarity of illustration;

FIG. 8 is a top plan view of the interface connector of FIG. 7;

FIG. 9 is a left end elevation of the interface connector of FIG. 7;

FIG. 10 is an enlarged horizontal section, taken along line 10—10 of FIG. 1 showing the interface of the laser light source with the single optical fiber and the interface of the camera with the optical bundle;

FIG. 11 is a front elevation of the structure shown in FIG. 10, with parts broken away for clarity of illustration;

FIG. 12 is a top plan view of the structure of FIG. 10 showing further details of the adjusting devices; and FIG. 13 is a block diagram of the circuitry within the remote control unit.

BEST MODE FOR CARRYING OUT THE INVENTION

Figure 1:
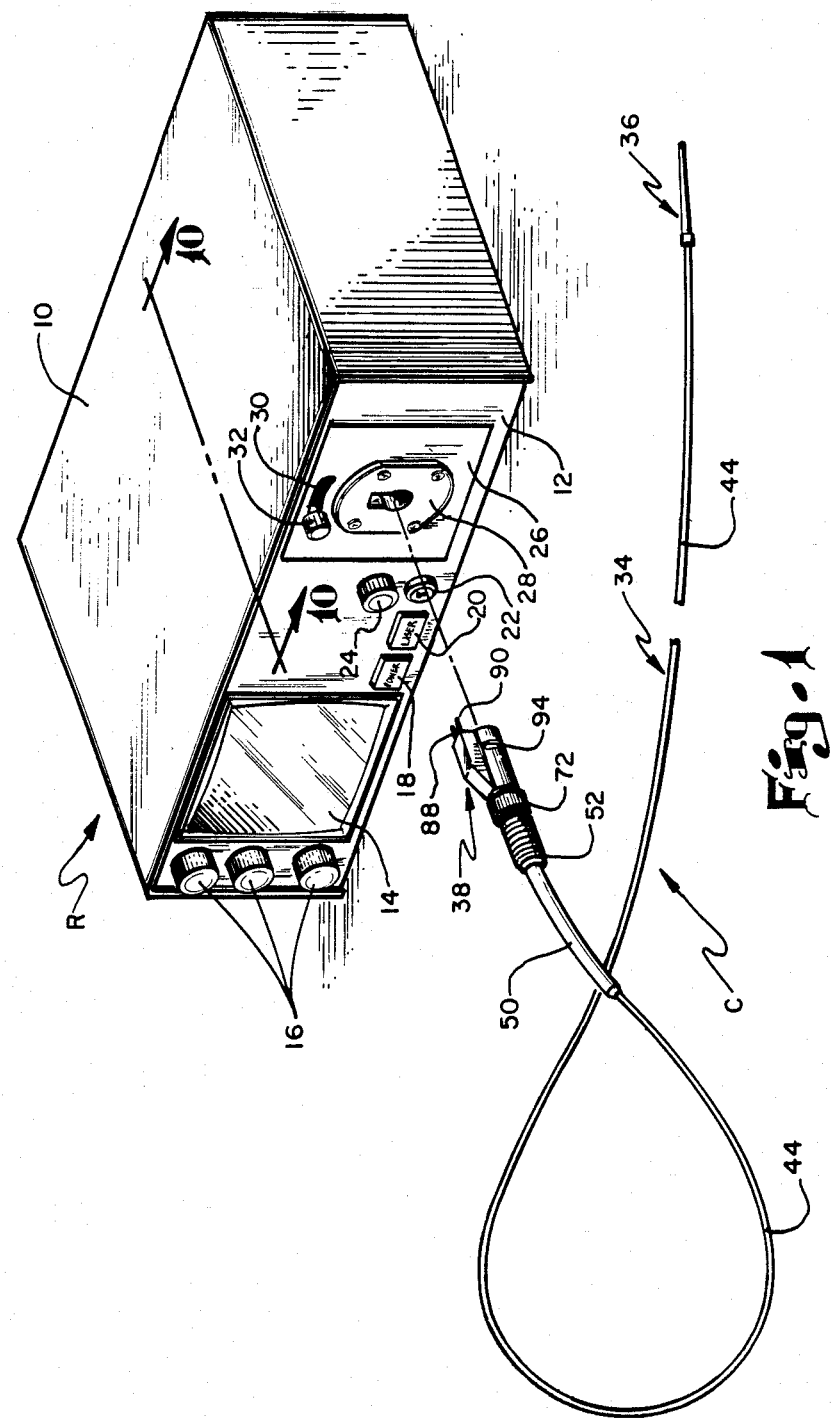
FIG. 1 is a perspective view of the laser endoscope constructed in accordance with this invention.

In accordance with this invention, a laser endoscope constructed in accordance with this invention is illustrated in FIG. 1. The endoscope comprises a remote control and viewing unit R to which a cable assembly C is removably connected. The remote unit R includes a housing 10 which has a front panel 12 in which viewing monitor 14 is mounted. To the left of the viewing screen are several knobs 16 which provide standard adjustments such as "contrast", "vertical hold" and "brightness". To the right of the screen is an on/off power switch 18 and an on/off switch 20 to energize a laser diode in housing 10. A key lock 22 is provided which must be unlocked to make either of switches 18 and 20 operable and initiates a laser delay. Above the key lock 22 is a focusing knob 24 for focusing the image on viewing screen 14, as will be discussed in more detail below. At the right end of front panel 12 is a face plate 26 in which a receptacle 28 is provided for establishing an interface between remote unit R and the cable assembly C, as will be discussed in more detail. Above receptacle 28 is an arcuate slot 30 in which a knob 32 can be moved from one end to the other to select a laser fiber through which a beam of laser light is to be directed. This feature will also be discussed in more detail below.

A cable assembly C includes a cable 34 having a tip 36 on the distal end for insertion into a body cavity and an interface connector 38 on the proximate end of the device for plugging into receptacle 28 of remote unit R.

Referring again to FIG. 1, the general operation of the laser endoscope can be understood. In this regard, by use of an appropriate key (not shown) in key lock 22, power button 18 can be pressed to turn on the power to viewing monitor 14. An electrical interlock is provided to prevent the activation of the laser until the interface connector 38 is inserted into receptacle 28. The laser diode can be activated by pressing button 20. Knob 32 will be placed in one of the alternate end positions along arcuate slot 30 so that the laser light beam will be projected along one of two single fibers which form part of cable assembly 34 and will be described in detail below. Once the appropriate selection has been made, the interface connector 38 can be inserted in receptacle 28 and tip 36, as well as a portion of cable assembly 34, can be inserted into the body of the patient either through a natural body canal leading to the area to be investigated or through a needle that has been inserted into the body at an appropriate location. For example, tip 36 and cable assembly 32 can be inserted in the urinary canal to investigate the bladder or kidneys. Because of the micro-thin diameter of the cable assembly, this can be accomplished with little or no discomfort to the patient. Alternatively, it can be inserted through a needle through the abdominal wall, and this may be done with the use of local anesthetic. With this device the physician can investigate portions of the body which either were not previously accessible or which were accessible only through the use of invasive operative techniques causing much trauma and discomfort to the patient. By way of example, the device can be inserted into the arteries and veins; in the brain; in the spine; and the joints. Most procedures for which this invention is intended can be performed on an outpatient basis or with a very minimal hospital stay.

Once tip 36 has been positioned at the site, the laser button 20 can be activated to energize the laser diode so that the laser light is projected through the single fiber to the site to illuminate it. The reflected light and image from the site is reflected back through the cable assembly for viewing on screen 14. The knobs 16 can be appropriately adjusted to provide the desired brightness, contrast and vertical hold. Also, knob 24 can be adjusted to bring the image into proper focus. Additionally, other physicians can view the screen along with the doctor whereby the device can serve to provide a means whereby more than one physician can be consulted concerning the condition existing within the body and additionally the device can be used as a training tool for students or other doctors. An output port (not shown), which is TV compatable, is provided for video recording.

Referring to FIGS. 2-9, the details of the cable assembly C can be seen. Cable 34 can be of any desired length but typically might be on the order of 1.0 to 1.5 meters in length. Along the center of cable 34, as best seen in FIG. 3, is a coherent fiber bundle 40 for transmitting an image from the site in the body cavity back to the viewing screen 14. This coherent fiber bundle can be extruded together during manufacture wherein the individual fibers adhere to each other along their peripheral edges and are coated with a silica coating and a jacket 42 which may be made of Teflon or PVC or some other similar material. Conveniently, coherent fiber bundle 40 can comprise anywhere from 10,000 to 50,000 individual fibers having a numerical aperture of 0.28 and having a core diameter of approximately 4 microns, the overall diameter with jacket 42 being approximately 0.5 to 2.5 millimeters. A space is provided between inner jacket 42 and an outer jacket 44 wherein a single laser fiber 46 and a redundant laser fiber 48 run spirally from interface connector 38 at the proximate end of cable assembly C to tip 36 on the distal end of cable assembly C. This outer jacket 44 can also be made of a fluorocarbon material such as Teflon, or PVC. Finally, an outer protective sheathing is provided along a portion of the length of outer jacket 44 and may be made of a fabric braid PVC covering or may be a flexible steel covering. The length of the cable extending beyond sheathing 50 can be on the order of 15 to 20 cm. At the end of the cable, adjacent interface connector 38, a strain relief coil spring 52 is provided having a length on the order of 7 to 9 mm. If desired, additional tubular passageways 54 can be provided in outer cover 44 for directing $CO_2$ gas or other fluid from a suitable source located in or adjacent to remote unit R through tip 36 to the desired site in the body cavity to blow away or wash away body fluids such as blood so that the particular area of the site to be viewed can be seen. The total diameter of outer jacket 44 will be on the order of 1.5 to 3.5 mm. whereas the outer diameter of sheathing 50 will be on the order on 5 to 6 mm. However, the sheathing portion will never be inserted into the body cavity and therefore this larger size is not objectionable.

Advantageously, a third, single laser fiber, such as fiber 53 shown in phantom in FIGS. 3 and 4, can be provided for use in laser treatment. For example, a second laser such as an argon laser could be provided in remote unit R and optically coupled with fiber 53 for performing laser surgery at the investigative site. Laser light for this purpose in the 500 nm. range has been found to be satisfactory.

As best seen in FIGS. 5 and 6, tip 36, which can be made of stainless steel, has a central bore 56 and a tapered outer side wall 58. The distal end of coherent fiber bundle 40 extends into bore 56 and terminates in a polished surface 59. Jackets 42 and 44 are foreshortened and received in a recess 60 in the proximate end of tip 36. The remainder of bore 56 is for locating a lens system which is illustrated by lenses 62. While only a pair of lenses have been shown it will be understood that the entire volume of bore 56 from the distal ends of optical fiber bundle 40 to planar window 64 can be filled with lenses if necessary. Lenses which provide 15, wide angle magnification have been found to be suitable. These lenses are for the purpose of focusing an image reflected from the body cavity so that this image can be transmitted by coherent fiber bundle 40 back to remote unit R. It may be that a lens will be positioned in the place of planar window 64, which can then be omitted.

A suitable adhesive, not shown, can be provided in recess 60 for joining the jackets 42 and 44 thereto and to prevent moisture from entering tip 36. As can best be seen in FIG. 6, jet openings 66 are positioned around the end of tip 36 and communicate with passageways 54 in outer jacket 44 so that $CO_2$ gas or other fluid can be expelled through the jet openings to clear away any blood or other body fluids that might interfere with the illumination and reflection of the image of the area of the body cavity being viewed.

As pointed out above, the proximate end of cable 34 extends through interface connector 38. Conveniently, as best seen in FIG. 7, the coherent fiber bundle 40 extends completely through connector 38 and has a polished end surface 67 which is coterminous with end face 68 of interface connector 38, as shown. Jackets 42 and 44 extend a short distance into a recess 69 in connector 38, as shown. Conveniently, strain relief spring 52 includes a flange 70 by which it is held in place by a lock nut 72 received over threaded neck 74 on interface connector 38.

A passageway 76 extends along the upper edge of the neck and communicates with upwardly extending passageway 78 which in turn connects divergent passageways 80 and 82 which in turn interconnect with longitudinal passageways 84 and 86, respectively. Advantageously, spaced above polished end 67 of coherent fiber bundle 40 are a pair of laterally spaced fiber optic pins 88 and 90, respectively. Laser fibers 46 and 48 have been omitted from FIGS. 7 and 8 for clarity of illustration. However, it will be understood that both fibers will extend through passageways 76 and 78 and that laser fiber 46 will then diverge through divergent pathway 80 and along horizontal pathway 84 and be connected to fiber optic pin 88. Similarly, redundant fiber 48 will pass through passageways 76 and 78 and then diverge through divergent passageway 82 and longitudinal passageway 86 to be connected to fiber optic pin 90.

Conveniently, the shape of the opening in receptacle 28 matches that of interface connector 38 to specifically and positively align interface connector 38 within receptacle 28. Interface connector 38 includes a pair of locking grooves 92 and 94 on opposite sides thereof which releasably lock and hold the interface connector within receptacle 28. It should also be understood that optic fiber pins 88 and 90 are exactly aligned with the respective laser fiber 46 and redundant fiber 48 so that when a laser beam of light is projected through the pins, it will achieve maximum power transfer. This enhances the total amount of light which can be provided at tip 36. Means (not shown) can be provided to control the laser power.

Turning now to FIGS. 10, 11 and 12, further details of the remote control unit R can be seen. For example, locking grooves 92 and 94 cooperate respectively with ball detents 96 and 98, which are held in place by springs 100 and 102, respectively mounted in recesses 104 and 106, respectively.

A slide member 108 is mounted for lateral sliding movement in face plate 26 and includes a rearwardly extending optical adapter 110 which receives an illuminator bundle 112 in socket 113 and has optical alignment with laser light beam 114 of diode laser 116. A laser providing light in the infrared and near infrared wavelengths will provide the most illumination at the site. By way of example, light in the range of 790 nm to 860 nm has been found to be satisfactory. The forward end of optical adapter 110 has a socket 117 for receiving selectively either fiber optic pin 88 or 90. As shown in FIG. 10, pin 90 is shown as being positioned in the socket, as it would be if the positioning knob is in the position shown in FIG. 11. Dummy sockets 118 and 119 may be provided on opposite sides of socket 117 to receive the pin which is not in use. Conveniently, a lever arm 120 is connected to knob 32 by knob shaft 122 and is pivoted about a pivot pin 124 mounted in face plate 26. The lower end of arm 120 is bifricated to form a slot 126, seen in FIG. 11, through which a pin 128 which is connected to slide 108 extends. As previously mentioned, when the lever arm is in the position shown in FIG. 11, socket 118 will be aligned with fiber optic pin 90. However, when the lever arm is moved to the dotted line position shown in FIG. 11, socket 119 will then be aligned with optic fiber pin 88. Thus, either single laser fiber 46 or redundant fiber 48 can be selected for projecting the beam of laser light. Pin 117 must be precisely aligned with laser beam 114 to provide maximum coupling and preserve the integrity of the laser beam. This arrangement maximizes the amount of light available at the site. The purpose of the two fibers is for redundancy in the event that one or the other of the fibers breaks. Thus, it does not matter in which position the lever arm is placed so long as the fiber which is placed actively in the system does not have a discontinuity which would prevent operation of the device. In that unlikely event, the interface connector 38 need merely be withdrawn from receptacle 28 and lever 32 moved to the opposite position to locate socket 118 to receive the fiber optic pin for the other single laser fiber.

A stationary lens tube 130 is aligned with proximate end of coherent fiber bundle 40 when interface connector 38 is in place. This tube can include one or more lenses such as lenses 132 and 134. This lens system serves to project the image transmitted by coherent fiber bundle 40 to camera 136 which has a forwardly projecting focal adapter 138 in to which the end of optical assembly 130 is slidably received. A dust and light shield 139 is provided on the end of adapter 138. Conveniently, camera 136 is mounted for back and forth movement on spaced parallel support rods 140 and 142 respectively mounted in a frame within remote control unit R. A rack 144 is mounted longitudinally on the bottom of the camera and is connected to a gear or pinion 146. The gear, in turn, is connected to a shaft 148 which may have a bevel gear 150 on the outer end thereof. Bevel gear 150 meshes with a second bevel gear 152 on shaft 154 connected to focusing knob 24. Thus, by turning focusing knob 24 one way or the other, the camera can be moved back and forth until the image projected therein is brought into proper focus for viewing on screen 14.

A block diagram of the remote control unit is illustrated in FIG. 13 showing diagramatically the general arrangement of all of the electronic elements which make up the remote control unit R and which are standard off-of-the-shelf items available to one skilled in the art for performing the video imaging described.

From the foregoing, the advantages of this invention are readily apparent. A device has been provided which has a micro-thin probe that can be inserted into the human body in almost any desired location to observe a condition which exists at that location. Such positioning of the device can be done, in many cases, through existing body canals. In other instances, it can be inserted through a small needle which can be accomplished by the use of only local anesthetic. Furthermore, with the remote control unit, a means is provided for displaying on a monitor an image of the interior of the body cavity at the desired location for the operating physician to see as well as other physicians and persons in attendance. A single laser light beam can be used to illuminate the interior of the body cavity at the desired site by the use of a single laser light beam, and particularly a light beam in the infrared or near infrared spectrum. This is possible by so precisely aligning the laser light beam with the single laser fiber to assure maximum coupling and preserve the integrity of the laser beam. Furthermore, the coherent optical bundle provides a means for transmitting the reflected image from the site to the camera. To enhance this projection a lens system is provided at the site within the probe and at the other end of the optical cable in the remote control unit. A novel interface provides for the transmission of both the laser light and the reflected light image from the site to the camera. Also, means can be provided, such as passageways for introducing jets of carbon dioxide gas or other fluid for clearing away blood or other body fluids from the site area to enhance viewing. It will also be understood that an additional laser light source could provide laser light of sufficient energy through one or more fibers either in or along the coherent bundle for actually performing operative procedures as is well understood by one skilled in the art. Finally, the endoscopic cable can be installed on one side of a grasping tool, such as forceps so that the surgeon can see and grasp an element which is to be removed, such as a kidney stone.

It will be understood that the term "micro-thin" as used herein shall mean and refer to a cable assembly having a diameter which does not exceed 3.5 mm.

The invention has been described in detail with particular reference to preferred embodiments thereof, but it will be understood that variations and modifications can be effected within the spirit and scope of the invention.

What is claimed is:

1. A remote viewing unit for use with a laser endoscope, said unit comprising:
    a TV camera;
    a viewing monitor for displaying an image of the image viewed by said TV camera;
    an optical cable interface including optical focus means for focusing an image from an optical cable on said TV camera;
    a laser diode for providing a beam of light to an optical fiber; and
    a laser fiber interface for aligning a light beam from said laser diode with the optical fiber.

2. A remote viewing unit, as claimed in claim 1, wherein said optical focus means includes:
    a stationary optical system within said remote unit with which said optical cable is alignable; and
    means to movably adjust said camera with respect to said stationary optical system to focus an image from said optical cable.

3. A remote viewing unit, as claimed in claim 1, further including:
    socket means in said laser fiber interface for selectively receiving an optic fiber pin connected to the end of one of two single optic fibers to align the selected one of them with the beam of light from said laser diode; and means for selectively shifting said socket means for alignment with the desired one of said pins prior to insertion of said interface connector.

4. An endoscopic cable assembly for use in viewing and/or treatment within body cavities by non-surgical or micro-surgical procedures, said cable assembly including:
- a coherent multi-fiber optical cable of micro-thin diameter having a planar distal end for insertion into a body cavity and a planar proximate end;
- optical lens means at the distal end of said optical cable to focus an image of a portion of the cavity on said distal end of said optical cable for transmission therethrough;
- a single optical fiber having a distal end adjacent said distal end of said optical cable and a proximate end adjacent said proximate end of said optical cable;
- an interface connector attached to said proximate end of said optical cable and said single fiber for removable attachment to a remote unit for respectively aligning said proximate end of said optical cable with an image display device in the remote unit to provide a viewable image of a portion of the body cavity, and aligning said proximate end of said single fiber with a light beam from a light source in the remote unit.

5. A cable assembly, as claimed in claim 4, further including:
- a redundant optical fiber having a distal end adjacent said distal end of said optical cable and proximate end adjacent said proximate end of said optical cable.

6. A cable assembly, as claimed in claim 5, further including:
- a pair of spaced optic fiber pins in said interface connector aligned respectively with the ends of said single optic fiber and said redundant fiber to be received in sockets in the remote unit.

7. A cable assembly, as claimed in claim 5, further including:
- at least one tubular passageway extending along said optical cable from its proximate end to its distal end for supplying a fluid to temporarily clear away blood or other matter at the viewing site within the body cavity to enhance viewing.

8. A cable assembly, as claimed in claim 7, further including:
- a plurality of said passageways equally spaced around said optical cable.

9. A cable assembly, as claimed in claim 5, wherein: said single fiber and said redundant fiber are spirally wound around said optical cable.

10. A cable assembly, as claimed in claim 9, wherein: said distal ends of said single fiber and said redundant fiber are adjacent said optical lens means.

11. A cable assembly, as claimed in claim 10, further including:
- an inner jacket surrounding said optical cable, said single fiber and said redundant fiber being wound around the outside of said inner jacket; and
- an outer jacket surrounding said inner jacket and said single fiber and said redundant fiber.

12. A cable assembly, as claimed in claim 11, further including:
- a protective sheath around said outer jacket extending from said proximate ends to a point spaced from said distal ends a distance at least equal to the length of said optical cable inserted into a body.

13. A cable assembly, as claimed in claim 11, wherein said inner and outer jackets terminate short of said distal ends of said optical cable and said single fiber and redundant fiber and wherein said distal end of said optical cable terminates short of said distal ends of said single fiber and said redundant fiber, said cable assembly further including:
- a tubular tip having a central passageway lying along an axis with a first end attached to said distal end of said jackets and a second end coterminous with said distal ends of said single fiber and said redundant fiber.

14. A cable assembly as claimed in claim 13, wherein: said distal end of said optical cable extends into said central passageway; and
said optic lens means is positioned within said passageway between said distal end of said optical cable and said second end of said tip.

15. A cable assembly, as claimed in claim 14, wherein: said tip is tapered from said first end to said second end; and
said single fiber and said redundant fiber extend through at least one passageway which is offset from the axis of said central passageway.

* * * * *

UNITED STATES PATENT AND TRADEMARK OFFICE
CERTIFICATE OF CORRECTION

PATENT NO. : 4,754,328

DATED : June 28, 1988

INVENTOR(S) : James D. Barath and Steven K. Case

It is certified that error appears in the above-identified patent and that said Letters Patent are hereby corrected as shown below:

Delete Columns 7 and 8 of the patent in their entirety and insert the following:

--optical adapter 110 has a socket 117 for receiving selectively either fiber optic pin 88 or 90. As shown in Figure 10, pin 90 is shown as being positioned in the socket, as it would be if the positioning knob is in the position shown in Figure 11. Dummy sockets 118 and 119 may be provided on opposite sides of socket 117 to receive the pin which is not in use. Conveniently, a lever arm 120 is connected to knob 32 by knob shaft 122 and is pivoted about a pivot pin 124 mounted in face plate 26. The lower end of arm 120 is bifurcated to form a slot 126, seen in Figure 11, through which a pin 128 which is connected to slide 108 extends. As previously mentioned, when the lever arm is in the position shown in Figure 11, socket 118 will be aligned with fiber optic pin 90. However, when the lever arm is moved to the dotted line position shown in Figure 11, socket 119 will then be aligned with optic fiber pin 88. Thus, either single laser fiber 46 or redundant fiber 48 can be selected for projecting the beam of laser light. Pin 117 must be precisely aligned with laser beam 114 to provide maximum coupling and preserve the integrity of the laser beam. This arrangement maximizes the amount of light available at the site. The purpose of the two fibers is for redundancy in the event that one or the other of the fibers breaks. Thus, it does not matter in which position

UNITED STATES PATENT AND TRADEMARK OFFICE
CERTIFICATE OF CORRECTION

PATENT NO. : 4,754,328

DATED : June 28, 1988

INVENTOR(S) : James D. Barath and Steven K. Case

It is certified that error appears in the above-identified patent and that said Letters Patent are hereby corrected as shown below:

the lever arm is placed so long as the fiber which is placed actively in the system does not have a discontinuity which would prevent operation of the device. In that unlikely event, the interface connector 38 need merely be withdrawn from receptacle 28 and lever 32 moved to the opposite position to locate socket 118 to receive the fiber optic pin for the other single laser fiber.

A stationary lens tube 130 is aligned with proximate end of coherent fiber bundle 40 when interface connector 38 is in place. This tube can include one or more lenses such as lenses 132 and 134. This lens system serves to project the image transmitted by coherent fiber bundle 40 to camera 136 which has a forwardly projecting focal adapter 138 in to which the end of optical assembly 130 is slidably received. A dust and light shield 139 is provided on the end of adapter 138. Conveniently, camera 136 is mounted for back and forth movement on spaced parallel support rods 140 and 142 respectively mounted in a frame within remote control unit R. A rack 144 is mounted longitudinally on the bottom of the camera and is connected to a gear or pinion 146. the gear, in turn, is connected to a shaft 148 which may have a bevel gear 150 on the outer end thereof. Bevel gear 150 meshes with a second bevel gear 152 on shaft 154 connected to focusing knob 24. Thus, by turning focusing knob 24 one way or the other, the camera can be moved back and forth until the image projected therein is brought into proper focus for viewing on screen 14.

UNITED STATES PATENT AND TRADEMARK OFFICE
CERTIFICATE OF CORRECTION

PATENT NO. : 4,754,328

DATED : June 28, 1988

INVENTOR(S) : James D. Barath and Steven K. Case

It is certified that error appears in the above-identified patent and that said Letters Patent are hereby corrected as shown below:

A block diagram of the remote control unit is illustrated in Figure 13 showing diagramatically the general arrangement of all of the electronic elements which make up the remote control unit R and which are standard off-of-the-shelf items available to one skilled in the art for performing the video imaging described.

From the foregoing, the advantages of this invention are readily apparent. A device has been provided which has a micro-thin probe that can be inserted into the human body in almost any desired location to observe a condition which exists at that location. Such positioning of the device can be done, in many cases, through existing body canals. In other instances, it can be inserted through a small needle which can be accomplished by the use of only local anesthetic. Furthermore, with the remote control unit, a means is provided for displaying on a monitor an image of the interior of the body cavity at the desired location for the operating physician to see as well as other physicians and persons in attendance. A single laser light beam can be used to illuminate the interior of the body cavity at the desired site by the use of a single laser light beam, and particularly a light beam in the infrared or near infrared spectrum. This is possible by so precisely aligning the laser light beam with the single laser fiber to assure maximum coupling and preserve the integrity of the laser beam. Furthermore, the coherent optical bundle provides a means for transmitting the reflected image from the site to

UNITED STATES PATENT AND TRADEMARK OFFICE
CERTIFICATE OF CORRECTION

PATENT NO. : 4,754,328
DATED : June 28, 1988
INVENTOR(S) : James D. Barath and Steven K. Case It is certified that error appears in the above-identified patent and that said Letters Patent are hereby corrected as shown below:

the camera. To enhance this projection a lens system is provided at the site within the probe and at the other end of the optical cable in the remote control unit. A novel interface provides for the transmission of both the laser light and the reflected light image from the site to the camera. Also, means can be provided, such as passageways for introducing jets of carbon dioxide gas or other fluid for clearing away blood or other body fluids from the site area to enhance viewing. It will also be understood that an additional laser light source could provide laser light of sufficient energy through one or more fibers either in or along the coherent bundle for actually performing operative procedures as is well understood by one skilled in the art. Finally, the endoscopic cable can be installed on one side of a grasping tool, such as forceps so that the surgeon can see and grasp an element which is to be removed, such as a kidney stone.

It will be understood that the term "micro-thin" as used herein shall mean and refer to a cable assembly having a diameter which does not exceed 3.5 mm.

The invention has been described in detail with particular reference to preferred embodiments thereof, but it will be understood that variations and modifications can be effected within the spirit and scope of the invention.

UNITED STATES PATENT AND TRADEMARK OFFICE
CERTIFICATE OF CORRECTION

PATENT NO. : 4,754,328

DATED : June 28, 1988

INVENTOR(S) : James D. Barath and Steven K. Case

It is certified that error appears in the above-identified patent and that said Letters Patent are hereby corrected as shown below:

We claim:
1. A remote viewing unit for use with a laser endoscope, said unit comprising:
  a TV camera;
  a viewing monitor for displaying an image of the image viewed by said TV camera;
  an optical cable interface including optical focus means for focusing an image from an optical cable on said TV camera;
  a laser diode for providing a beam of light to an optical fiber; and
  a laser fiber interface for aligning a light beam from said laser diode with the optical fiber.

2. A remote viewing unit, as claimed in Claim 1, wherein said optical focus means includes:
  a stationary optical system within said remote unit with which said optical cable is alignable; and
  means to movably adjust said camera with respect to said stationary optical system to focus an image from said optical cable.

3. A remote viewing unit, as claimed in Claim 1, further including:
  socket means in said laser fiber interface for selectively receiving an optic fiber pin connected to the

UNITED STATES PATENT AND TRADEMARK OFFICE
CERTIFICATE OF CORRECTION

PATENT NO. : 4,754,328

DATED : June 28, 1988

INVENTOR(S) : James D. Barath and Steven K. Case

It is certified that error appears in the above-identified patent and that said Letters Patent are hereby corrected as shown below:

end of one of two single optic fibers to align the selected one of them with the beam of light from said laser diode; and--

Signed and Sealed this

Fourteenth Day of February, 1989

Attest:

DONALD J. QUIGG

Attesting Officer

Commissioner of Patents and Trademarks